(12) United States Patent
Ledergerber

(10) Patent No.: US 8,202,316 B2
(45) Date of Patent: Jun. 19, 2012

(54) MODULATING BUTTRESS SALINE MAMMARY PROSTHESIS

(76) Inventor: Walter J. Ledergerber, Anaheim, CA (US)

( * ) Notice: Subject to any disclaimer, the term of this patent is extended or adjusted under 35 U.S.C. 154(b) by 403 days.

(21) Appl. No.: 12/360,979

(22) Filed: Jan. 28, 2009

(65) Prior Publication Data

US 2009/0216323 A1 Aug. 27, 2009

Related U.S. Application Data

(60) Provisional application No. 61/024,405, filed on Jan. 29, 2008.

(51) Int. Cl.
*A61F 2/12* (2006.01)

(52) U.S. Cl. .......................................................... 623/8

(58) Field of Classification Search .................. 623/7–8
See application file for complete search history.

(56) References Cited

U.S. PATENT DOCUMENTS

| | | | |
|---|---|---|---|
| 2,542,619 A | 2/1951 | Bernhardt |
| 3,093,831 A | 6/1963 | Jordan |
| 3,293,663 A | 12/1966 | Cronin |
| 3,366,975 A | 2/1968 | Pangman |
| 3,559,214 A | 2/1971 | Pangman |
| 3,683,424 A | 8/1972 | Pangman |
| 3,852,833 A | 12/1974 | Köneke et al. |
| 3,971,381 A | 7/1976 | Gibson |
| 4,019,209 A | 4/1977 | Spence |
| 4,034,751 A | 7/1977 | Hung |
| 4,175,557 A | 11/1979 | Hung |
| 4,209,921 A | 7/1980 | Kochauf |
| 4,264,990 A | 5/1981 | Hamas |
| 4,289,125 A | 9/1981 | Hung |
| 4,428,082 A | 1/1984 | Naficy |
| 4,531,244 A | 7/1985 | Hamas |
| 4,559,254 A | 12/1985 | Suzuki |
| 4,571,749 A | 2/1986 | Fischell |
| 4,573,999 A | 3/1986 | Netto |
| 4,574,780 A | 3/1986 | Manders |
| 4,605,412 A | 8/1986 | LaForest et al. |
| 4,615,704 A | 10/1986 | Frisch |
| 4,643,733 A | 2/1987 | Becker |
| 4,648,880 A | 3/1987 | Brauman |
| 4,650,487 A | 3/1987 | Chaglassian |
| 4,651,721 A | 3/1987 | Mikulich et al. |
| 4,673,409 A | 6/1987 | Van Kampen |
| 4,685,447 A | 8/1987 | Iversen et al. |
| 4,741,941 A | 5/1988 | Englebert et al. |
| 4,743,480 A | 5/1988 | Campbell et al. |
| 4,772,287 A | 9/1988 | Ray et al. |
| 4,790,848 A | 12/1988 | Cronin |
| 4,795,472 A | 1/1989 | Crowninshield et al. |
| 4,816,339 A | 3/1989 | Tu et al. |

(Continued)

Primary Examiner — Suzette J Gherbi
(74) Attorney, Agent, or Firm — David B. Murphy; O'Melveny & Myers

(57) ABSTRACT

A saline-filled breast prosthesis has enhanced performance by virtue of having tactile characteristics approximating those of gel-filled implants. The invention retains all the benefits of the recognized safety profile, straight-forward construction, and broad clinical indications for saline implants. An enhanced implantable mammary prosthesis comprises a shell, a slurry filler compartment interior to the shell containing slurry filler, a fluid compartment, the fluid compartment being deformable from a neutral profile under pressure from the slurry filler and which recoils to the neutral profile when not under pressure, a reservoir, the reservoir being disposed external to the shell, the reservoir and fluid compartment being fluidically coupled by a port, and a limiting membrane region disposed between the fluid compartment and the reservoir.

41 Claims, 7 Drawing Sheets

U.S. PATENT DOCUMENTS

| | | | | |
|---|---|---|---|---|
| 4,865,603 | A | 9/1989 | Noiles | |
| 4,899,764 | A | 2/1990 | Gauger et al. | |
| 4,955,881 | A | 9/1990 | Eckenhoff | |
| 4,955,907 | A | 9/1990 | Ledergerber | |
| 4,960,425 | A | 10/1990 | Yan et al. | |
| 4,984,585 | A | 1/1991 | Austad | |
| 5,022,942 | A | 6/1991 | Yan et al. | |
| 5,026,394 | A | 6/1991 | Baker | |
| 5,141,581 | A | 8/1992 | Markham | |
| 5,146,933 | A | 9/1992 | Boyd | |
| 5,207,709 | A | 5/1993 | Picha | |
| 5,219,361 | A | 6/1993 | von Recum et al. | |
| 5,282,856 | A | 2/1994 | Ledergerber | |
| 5,447,535 | A | 9/1995 | Muller | |
| 5,534,023 | A * | 7/1996 | Henley | 623/8 |
| RE35,391 | E | 12/1996 | Brauman | |
| 5,584,885 | A | 12/1996 | Seckel | |
| 5,653,755 | A | 8/1997 | Ledergerber | |
| 5,658,330 | A * | 8/1997 | Carlisle et al. | 623/11.11 |
| 5,716,412 | A | 2/1998 | DeCarlo, Jr. et al. | |
| 5,723,006 | A * | 3/1998 | Ledergerber | 623/8 |
| 5,779,734 | A | 7/1998 | Ledergerber | |
| 5,824,081 | A * | 10/1998 | Knapp et al. | 623/23.72 |
| 5,892,621 | A | 4/1999 | McGregor et al. | |
| 6,083,262 | A * | 7/2000 | Caravel | 623/8 |
| 6,099,565 | A | 8/2000 | Sakura, Jr. | |
| 6,187,043 | B1 | 2/2001 | Ledergerber | |
| 6,228,116 | B1 | 5/2001 | Ledergerber | |
| 6,875,233 | B1 * | 4/2005 | Turner | 623/8 |
| 6,921,418 | B2 | 7/2005 | Ledergerber | |
| 7,081,136 | B1 * | 7/2006 | Becker | 623/8 |
| 2005/0080338 | A1 * | 4/2005 | Sirimanne et al. | 600/431 |
| 2009/0210056 | A1 * | 8/2009 | Forsell | 623/8 |
| 2010/0010627 | A1 * | 1/2010 | Matheny | 623/8 |
| 2010/0217388 | A1 * | 8/2010 | Cohen et al. | 623/8 |

* cited by examiner

MODULATING BUTTRESS SALINE MAMMARY PROSTHESIS

PRIORITY CLAIM

This application claims the benefit of and priority to U.S. Provisional patent application Ser. No. 61/024,405, entitled "Modulating Buttress Saline Mammary Prosthesis Gel Simulating Saline Implant", filed Jan. 29, 2008, hereby incorporated by reference as if fully set forth herein.

FIELD OF THE INVENTION

This invention relates to implantable prosthetic devices and to tissue expanders used in plastic and reconstructive surgery used to stretch tissues. More particularly, the invention relates generally to a preferably saline implant that simulates the properties of gel implants.

BACKGROUND OF THE INVENTION

Most tissue expanders and soft tissue-simulating implantable prostheses have been utilized to enhance or reconstruct the female breast. While success has been achieved across the spectrum of devices and procedures, the predictability of success has very often been a matter of intelligent guesswork by implanting surgeons. Despite the sometimes fortuitous selection of patients with low allergic response to polysiloxane implant fillers, the search for a broadly acceptable implant configuration has been protracted by differing implant shell and surface topographies, and by the range of quality of surgical outcomes. Silicone gel-filled implants, having the seductive ex vivo visual and tactile characteristics of clear transparency and gel consistency, have driven the "criteria" for such an implant rather than has the clinically more beneficial criterion of non-antigenicity.

Ultimately, it has become clear that silicone oils originating inside a gel-filled implant could manifest on the exterior surface of the shell, and being antigenic, could stimulate a self-protective response on the part of the patient. As a consequence, very dense tough scar tissue forms which serves to deform and severely harden what would otherwise be a soft breast. Such failures have stimulated a wider search for possible solutions including changes in surgical technique such as placing the implant, usually gel-filled silicone, into the sub-pectoral position. Sub-muscular placement of implants has increased the complication rate.

Complex multi-component implant constructions including textured shells, "protective" saline compartmentalization around silicone gel compartments, and baffling schemes and others have been tried and eventually rejected as being problematic for a variety of reasons. Likewise, triglyceride fillers and others have met similar fates.

Various other topologies, coverings and texturizing methods and structures have been contributed to the art. See for example my earlier U.S. Pat. No. 4,955,907 entitled "Implantable Prosthetic Device", and U.S. Pat. No. 6,228,116 entitled "Tissue Expander". Those patents are hereby incorporated by reference as if fully set forth herein.

Yet, a safer natural alternative, the saline-filled implant has always been available. Unfortunately, resistance to its broad adoption has been based on esthetic consideration both ex vivo and as implanted. Its acceptance has been limited by its less than satisfactory "off-clear" appearance, the propensity to wrinkle due to a stiff high density shell and the fact that normal saline filler itself offers little resistance to deformation and is too quick to propagate visible waves on deformation. Such features have often led to embarrassment for the patient. Thus, there is an ongoing need for an enhanced performance saline implant which simulates the tactile features and performance of a silicone elastomer gel-filled implant but which lacks the antigenicity of filler silicone oils.

SUMMARY OF THE INVENTION

An enhanced implantable mammary prosthesis comprises a shell and a slurry filler compartment interior to the shell containing slurry filler. A fluid compartment is in pressure transmissive contact with the slurry filler. The fluid compartment is deformable from a neutral profile under pressure from the slurry filler, and it recoils to the neutral profile when not under pressure. A reservoir is disposed preferably external to the shell. The reservoir and the fluid compartment are fluidically coupled by a port. A limiting membrane region is disposed between the fluid compartment and the reservoir to provide sufficient structural rigidity that the pressure transmission from the slurry filler can be effectively transmitted to the fluid compartment and in turn be relieved by expansion of the reservoir by fluid passing from the fluid space through the port. Optionally, additional structures may be provided on or in the fluid compartment to aid in the recoil of the fluid compartment.

In the preferred detailed embodiment, the combination of components including 1) a silicone elastomer shell which is compliant to the touch, but highly resistant to rupture due to abrasion and also resistant to the transudation of water-consistency diluents, 2) a slurry filler consisting of a biocompatible fluid, such as normal saline, and dense suspension preferably comprising a prodigious number of medical glass or biocompatible polymer micro-toroids or spheres, 3) a structure or buttress preferably comprising a sessile hollow silicone elastomer structure or buttress situated within and adhesively attached internal to the shell at the base, and 4) a lens-like reservoir being located external to the implant but in fluid communication with the structure or buttress which is located internal to the shell, with a thick limiting membrane interposed between the fluid compartment and the reservoir. The buttress preferably contains a buffered biocompatible fluid, such as normal saline, which is voided to the lens-like reservoir in order to accommodate deformation of the buttress under the influence of increased pressure in the slurry compartment. As pressure in the slurry compartment again decreases, the buttress assumes its original profile (rebounds) due to its relative stiffness and recoil, with the fluid in the reservoir being sucked back into the buttress.

The enhanced-performance slurry of the invention has increased viscosity due to the large number of individual particles within it in frictional interference with other like particles and the ratio of solid to liquid components. Buffered normal saline is the preferred fluid. The "solid-particulate" component ideally is comprised of a prodigious quantity of "closest-packing" diameters of medical glass spheres or biocompatible polymer spheres or micro-toroids which may be textured or metal-plated to enhance their performance. Besides frictional interference, electrostatic forces and surface tension influence overall viscosity. Amorphous glass "frit" can be admixed to increase friction, as well. Silver plated glass particles will additionally confer bacteriostatic properties to such a slurry. The slurry will have an ideal viscosity when it resembles that of thick toothpaste or thin bread dough.

Pat. No. 5,282,856. It illustrates a sessile normal saline-filled compartment adherent to the internal base of the implant surrounded and in contact with the contents of the surrounding volume, here a sponge. The saline-filled compartment here is visually analogous to the buttress in FIG. 3. My U.S. Pat. No. 5,282,856 is hereby incorporated by reference as if fully set forth herein.

Figure 1:
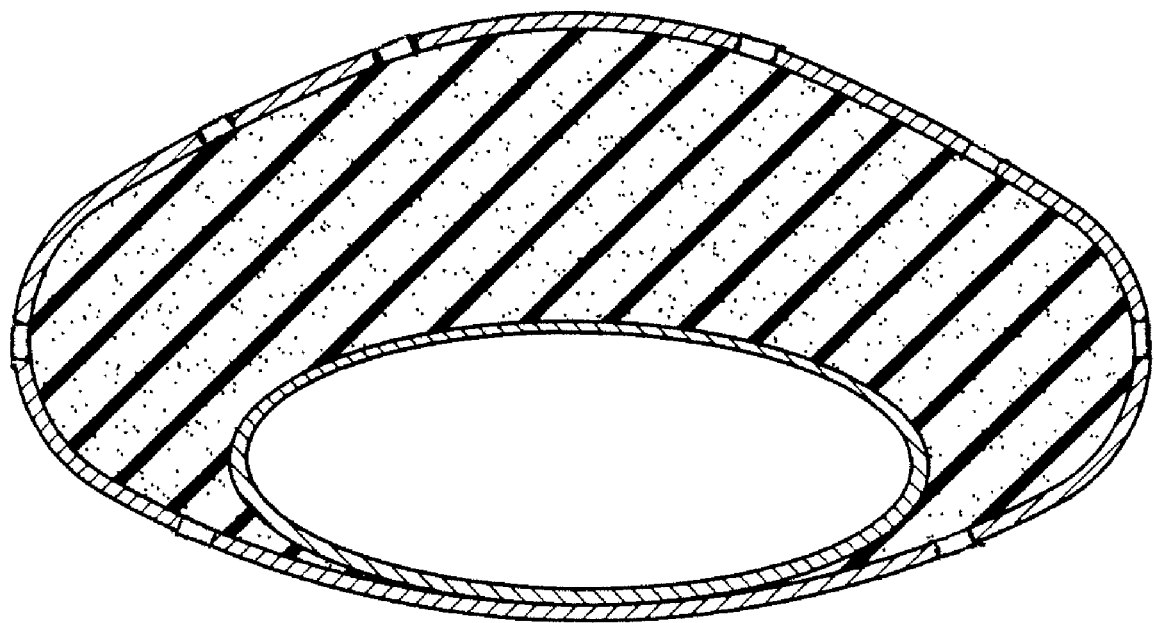
FIG. 1 is a vertical cross-section of a prior art multi-compartment saline implant, specifically FIG. 21 from my U.S.
Figure 2:
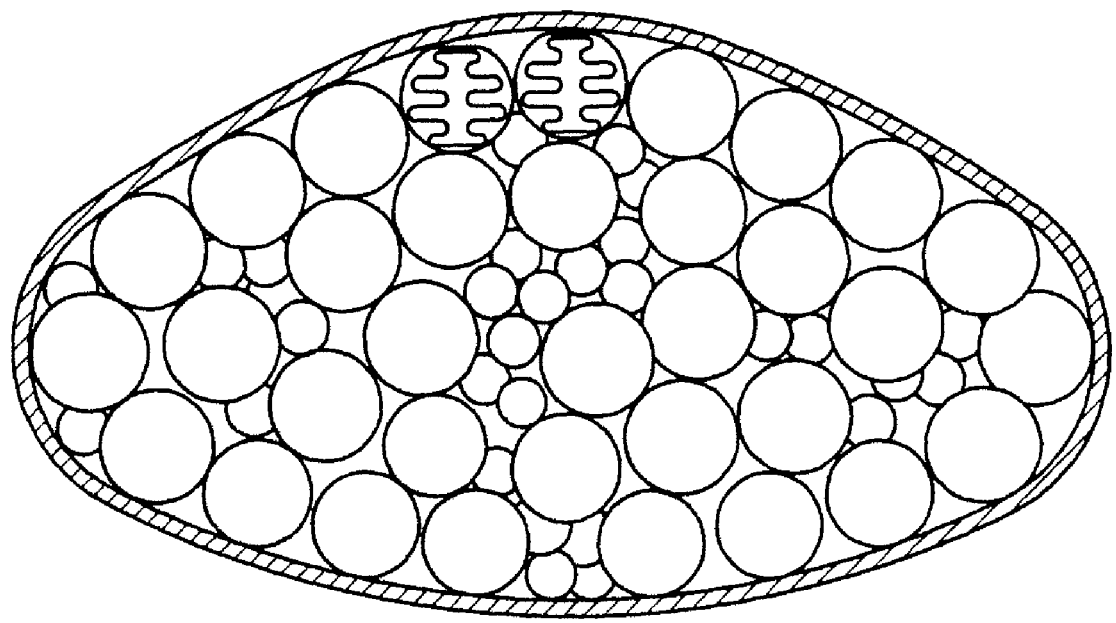

FIG. 2 is a vertical cross-section of a prior art saline implant, specifically FIG. 23 from my U.S. Pat. No. 5,282,856, whose entire volume is occupied by spheres of different diameters. The spheres here are analogous to the particulate elements comprising the slurry of FIGS. 3 and 6.

Figure 3:
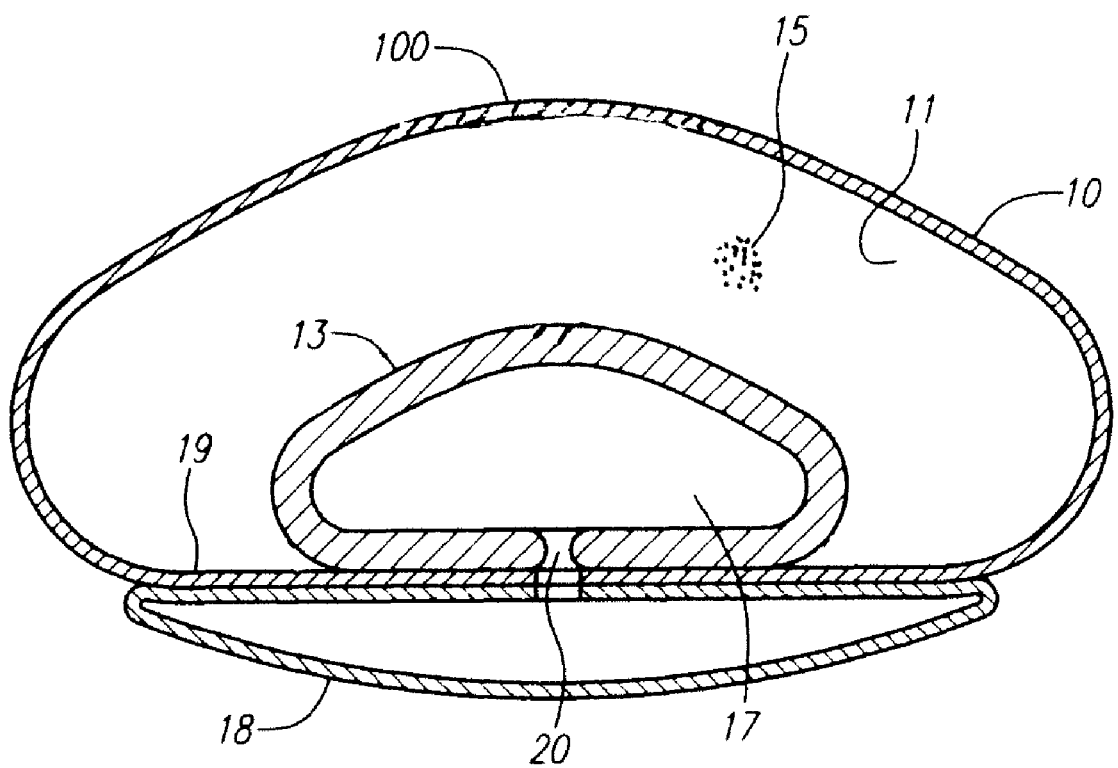

FIG. 3 is a vertical cross-section of the invention showing the implant, the shell, the slurry filler compartment, the reservoir and the limiting membrane region.

Figure 4:
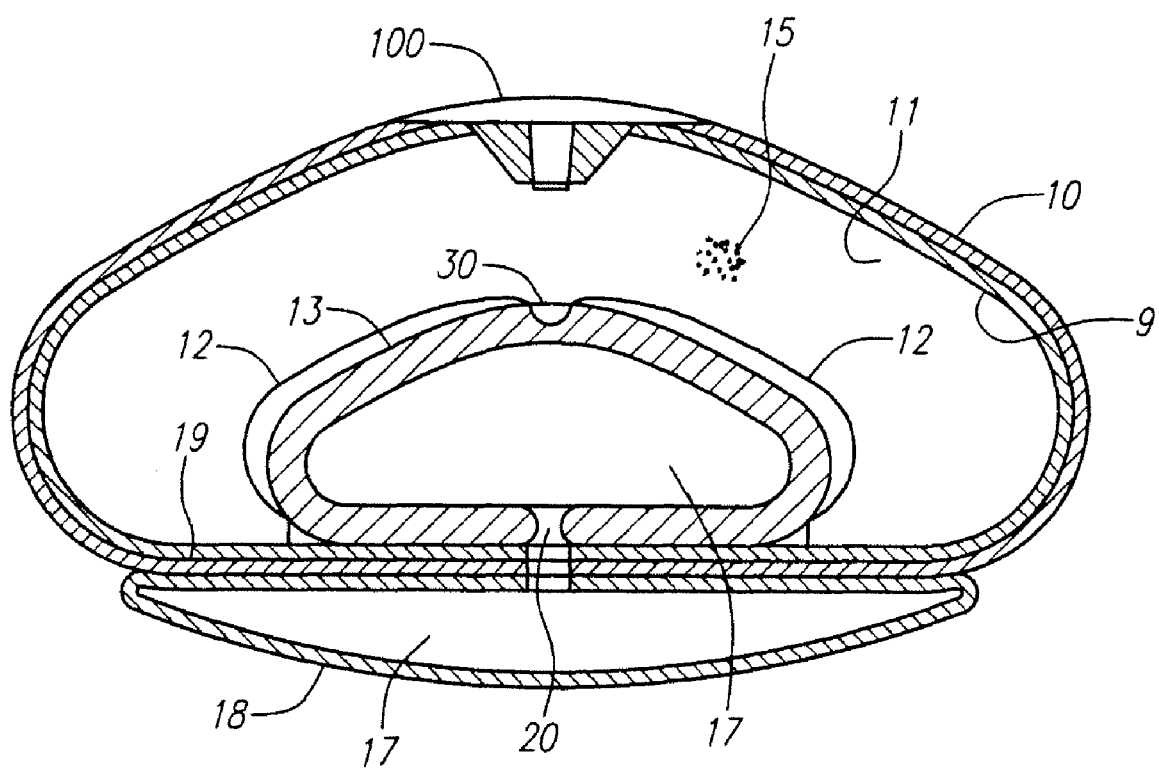

FIG. 4 is a vertical cross-section of one more detailed aspect of the invention showing the sessile nature of the normal saline-filled buttress and its attachment to the thick internal base of the implant as well as a side view of its relationship with the slurry-containing compartment and the lens-like normal saline-containing reservoir.

Figure 5:
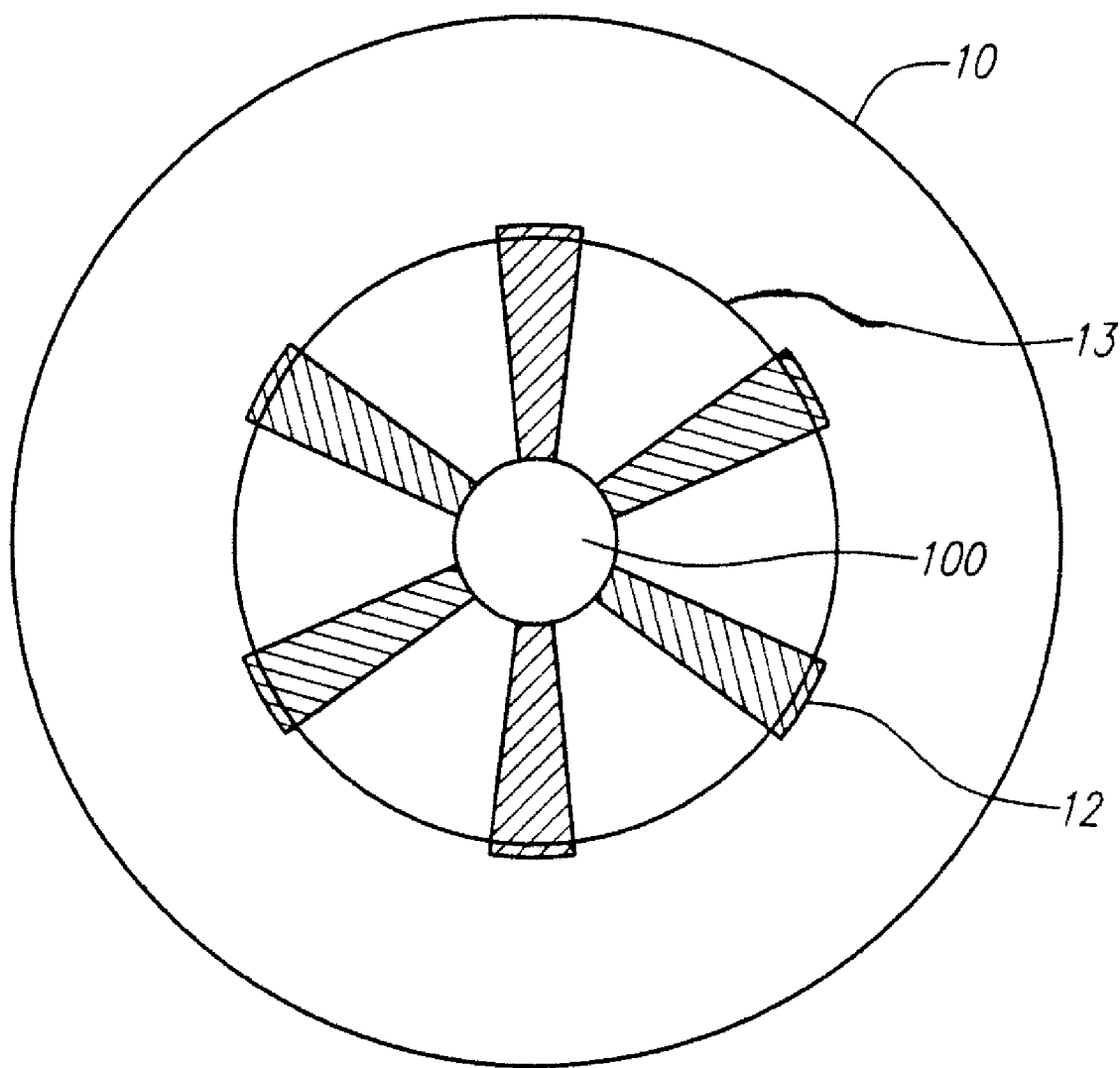

FIG. 5 is a transparent top view of the invention illustrating surface detail of the buttress and slurry fill port.

Figure 6:
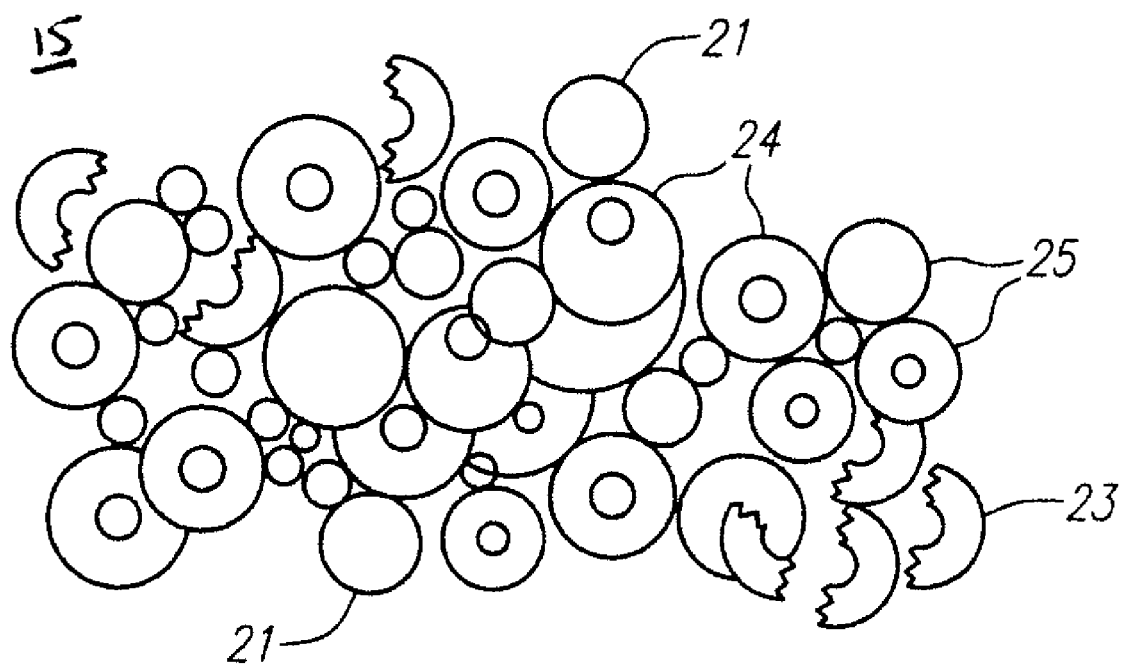

FIG. 6 is an illustration of particulate components of the slurry greatly magnified including spatial relationships and interference with one another.

Figure 7:
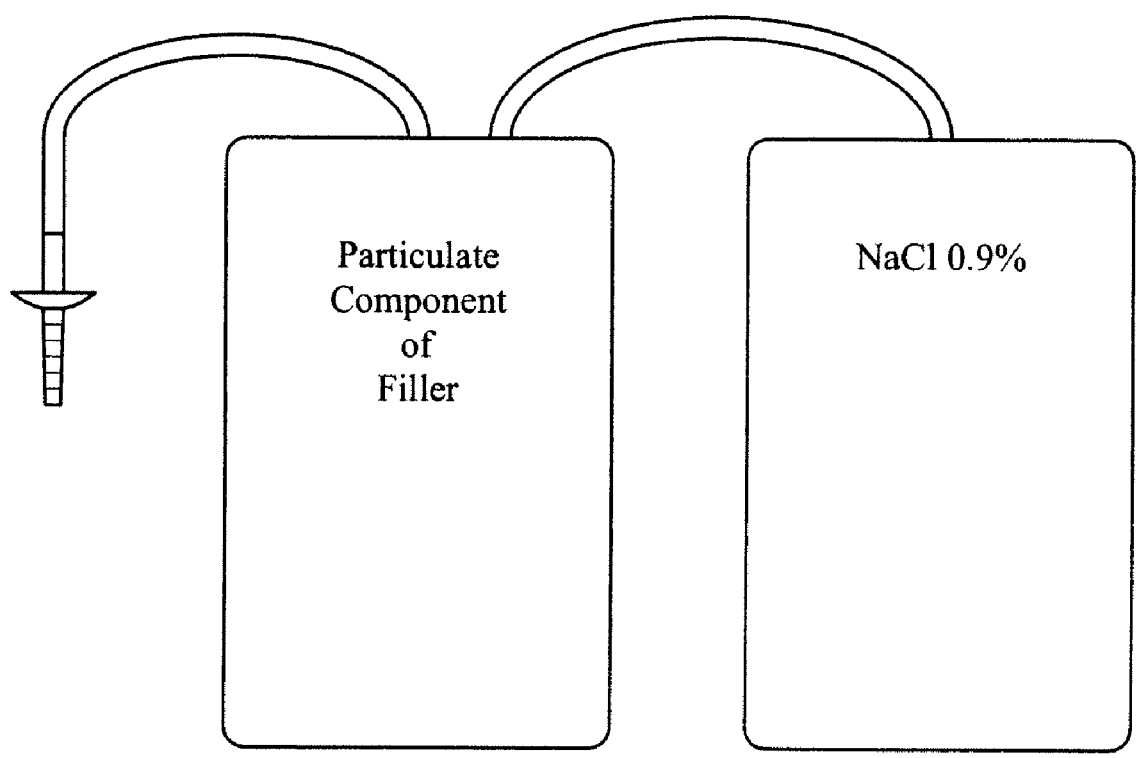

FIG. 7 is an illustration of a fill kit including attached bags, tubing, valves and solid and liquid components of slurry filler.

DETAILED DESCRIPTION OF THE INVENTION

The attached figures serve to illustrate the general and preferred embodiments of the invention. FIG. 3 shows a cross-section of the inventive implant in a general form. A shell 10 serves as the exterior surface of the implant. The shell 10 may be of a single material, or may be made of multiple layers (see, e.g., the embodiment of FIG. 4). Within the shell 10 is a slurry filler compartment 11 which is adapted to receive slurry filler 15 (shown enlarged in FIG. 6), or if the implant has been filled, will contain the slurry filler. The drawing of FIG. 3 and FIG. 4 only show a portion of the slurry filler for illustrative purposes, it being appreciated that the slurry filler would typically occupy the entirety of the slurry filler compartment 11 when fully filled. The slurry filler compartment 11 may either be an additional structure or may be the space defined by other structures such as the inside of the shell 10 and outside of the fluid compartment 13. A fluid compartment 13 is in pressure transmissive contact with the slurry filler. The fluid compartment 13 is deformable from a neutral profile under pressure from the slurry filler and which recoils to the neutral profile when not under pressure. The fluid compartment 13 contains an interior fluid space 17 adapted to hold, or if filled, holds the fluid. A reservoir 18 is disposed preferably external to the shell. The reservoir 18 and fluid space 17 are fluidically coupled such as by a port or tunnel 20. A limiting membrane region 19 is generally disposed between the fluid compartment 13 and the reservoir 18. While the limiting membrane region 19 may be a separate additional structure, such as an annular disk having a hole centered with the port 20, the limiting membrane region 19 may be formed from the materials located there, e.g., the shell 10, reservoir 18 and fluid compartment 13, all where they join at the back of the implant. The region 19 serves to provide sufficient structural rigidity that the pressure transmission from the slurry filler can be effectively transmitted to the fluid compartment 13 and in turn be relieved by expansion of the reservoir 18 by fluid passing from the fluid space 17 through the port 20. The comments made here regarding the general embodiment depicted in FIG. 3 also apply to the more detailed embodiment described, below.

FIG. 4 is a vertical cross section of the invention in a particular embodiment adapted for ease of manufacture. The implant shell 10 consists of a compliant silicone elastomer shell plus a laminated low bleed layer 9 adherent to the inner surface. The shell defines volume 11 which is occupied by slurry filler 15 (see also FIG. 6) and buttress or fluid compartment 13. The buttress is adhesively attached to a thick skirt 19 which is in turn adhesively attached at the center of the internal base of the shell 10, their central axes all coinciding with the thick limiting membrane which is interposed. Port 20 is a short tunnel connecting buttress 13 and reservoir 18 and passing through thick membrane 19. The reservoir 18 is lens-like in configuration and is delimited at its periphery by adhesive affixation to the thick skirt membrane 19.

The fluid in fluid space 17 is a biocompatible fluid, preferably 0.9% NaCl buffered to pH 7.0. and is also a component of the slurry filler 15. The fluid is located in both the fluid space 17 of the buttress 13 and reservoir 18. The fluid is preferably introduced into the volume 11 of slurry filler compartment through fillport 100 and then into the buttress 13 via syringe and hollow needle puncture. A measured volume is injected and the needle withdrawn. All air must be eliminated from this compartment. The needle puncture site on the buttress then is sealed with a liquid silicone patch 30 and later cured.

FIG. 5 illustrates the buttress 13 relationship to other structural components in a top "transparent view" of the implant with buttress 13 surface detail and ghosted slurry fillport 100 at the apex of the implant. The structures in FIG. 5 help clarify the terminology used herein. The term that buttress 13 refers to is to be understood to be the fluid compartment 13, which has the attributes described previously, namely that it is a structure deformable from a neutral profile under pressure from the slurry filler and which recoils to the neutral profile when not under pressure. The buttress structural member 12 in FIG. 5 adhered to the exterior of the fluid compartment or buttress 13 is meant to refer to buttress in the narrower sense of an additional structure provided to steady or support another structure. The buttress structural member 12 may be provided on the exterior of the fluid compartment or buttress 13 (as shown in FIG. 5) or may be internal to the fluid compartment or buttress 13.

FIG. 6 illustrates origins of frictional interference of particulates in the slurry filler 15. Slurry filler 15 is comprised of a mixture of buffered 0.9% NaCl and medical glass spheres 21 or micro-toroids 22 or biocompatible polymer structural equivalents in prodigious numbers. The globules or toroids may all be comprised of the same diameter or may be a mixture of diameters satisfying "closest packing" specifications. The solid component is essentially a powder of globules and toroids in the range ideally between 500 microns-2.0 mm. Amorphous "frit" 23 selected from the same materials serves to add friction. Such "closest packing" criteria allow for optimal friction. Other physical features of such an admixture optimized for performance include etched 24 and/or metal plated particulates 25. Operating also in the slurry are surface tension and electrostatic forces. The net viscosity is a function of all such factors operating together. Metal silver plating of particulates will confer antibiotic/bacteriostatic properties to the slurry.

Overall performance of the implant here will be defined as its ability to simulate a gel-filled implant. If shell 10 is indented, the Slurry filler 15 is caused to flow diffusely away from the area of deformation and toward the buttress and, in turn fluid 17. Fluid 17 is caused to move via tube 20 into reservoir 18. The lens-like reservoir partially fills and assumes a thicker lens-like configuration. The pulsion on the implant, by virtue of the slurry having a toothpaste-like consistency, modulates the propagation of pressure waves through it and along with the displaced saline 17 in the volume being transferred from the buttress 13 to the reservoir 18, achieves the modulation of applied external pressure and simulates the performance of a gel.

Upon release of the pressure on the implant, there is a reversal of the aforementioned sequence of events: Buttress 13 is constructed so as to maximize its recoil back to its original shape and in doing so "aspirates" fluid 17 and resumes its former volume, thus causing the whole implant profile and volume to be reestablished. The lens-like reservoir 18 has the capacity to distribute fluid over a wide area underneath the implant so that its volume expansion and contraction are hardly noticeable. Repeated pulsed stretching of scar tissue surrounding the implant during initial wound healing will result in an appropriately enlarged scar envelope around the implant.

As external pressure is relieved, and equilibrium reestablished, the patient's tissues again resume their former appearance.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

I claim:

1. An implantable mammary prosthesis comprising:
   a shell,
   a slurry filler compartment interior to the shell containing slurry filler,
   a hollow fluid compartment, the fluid compartment being deformable from a neutral profile under pressure from the slurry filler and which recoils to the neutral profile when not under pressure,
   a reservoir, the reservoir being disposed external to the shell, the reservoir and fluid compartment being fluidically coupled by a port, and
   a limiting membrane region disposed between the fluid compartment and the reservoir.

2. The implantable prosthesis of claim 1 wherein the shell comprises silicon elastomer.

3. The implantable prosthesis of claim 1 wherein the hollow fluid compartment is a silicone elastomer structure.

4. The implantable prosthesis of claim 1 wherein the reservoir is lens-shaped.

5. The implantable prosthesis of claim 1 wherein the fluid compartment includes a modulating buttress.

6. The implantable prosthesis of claim 1 wherein the slurry filler is comprised of the group including medical glass toroids, spheres and amorphous glass "frit", having a combination of particles ranging in diameter from 500 microns to 2.0 mm, resembling a powder suspended in normal saline.

7. The implantable prosthesis of claim 1 wherein the slurry comprises normal saline and chemically etched or silver plated particulate solids.

8. The implantable prosthesis of claim 1 wherein the slurry has a high ratio of medical glass particulate solids to normal saline so as to have a high viscosity resembling that of silicone elastomer gel or thick toothpaste.

9. The implantable prosthesis of claim 1 wherein the slurry filler is comprised of the group including biopolymer toroids, spheres and amorphous glass "frit", having a combination of particles ranging in diameter from 500 microns to 2.0 mm, resembling a powder suspended in normal saline.

10. The implantable prosthesis of claim 1 wherein the slurry comprises particulate elements of a number of differing diameters such that "nesting" or "closest packing" defines their spatial relationship.

11. The implantable prosthesis of claim 1 wherein the fluid compartment comprises a buttress consisting of a sessile hollow ovoid structure which is adherently located internally at the base pole of the implant and which is rigid or relatively deformable and compliant by changing the fluid volume contained within it.

12. The implantable prosthesis of claim 11 wherein the fluid compartment is made from a silicone elastomer molding with the necessary structural resiliency providing a high degree of recoil, and having a void within it which is in fluid communication with a reservoir.

13. The implantable prosthesis of claim 1 wherein the implant is pre-filled with slurry and normal saline.

14. The implantable prosthesis of claim 1 wherein the fluid compartment has a fluid capacity of approximate 20-35% of the fluid volume of the whole implant.

15. The implantable prosthesis of claim 11 wherein the slurry filler compartment and the fluid compartment buttress share a fluid access portal via the apical fillport and furthermore the buttress having a needle access point at the depression at the apex of the buttress and each having its own specified fluid.

16. The implantable prosthesis of claim 15 wherein the apical fillport includes a large enough diameter to permit the tubular introduction of the slurry.

17. The implantable prosthesis of claim 11 wherein the buttress serves as a major conditioner-modulator of the overall viscosity of the slurry filler by serving as a buttress against which induced fluid pressure waves in the implant are accelerated or retarded by virtue of its relative profile and susceptibility to deformation, or lack thereof, and which functions also to enable it to transfer to, or aspirate quantities of contained normal saline from an external reservoir adjoining the implant.

18. The implantable prosthesis of claim 1 wherein the fluid compartment includes molded ribs to aid in the structural recoil for transitioning between its deformed profile and its native/neutral profile.

19. The implantable prosthesis of claim 1 having a shape calibrated to resist excessive deformation and also the capacity to bleed-off or transfer fluid from inside the implant to a lens-like reservoir outside the implant.

20. The implantable prosthesis of claim 1 wherein the reservoir contains normal saline and communicates freely with the fluid compartment via a tube and the reservoir being lens-shaped and located below and outside the implant.

21. The implantable prosthesis of claim 1 wherein the fluid compartment has a unique fillport being a targetable depression located at the central apex of the fluid compartment, which point is capable of being penetrated by a hollow hypodermic needle to enable the introduction of normal saline into the buttress and also to extract any unwanted gas contained therein.

22. An implantable mammary prosthesis comprising:
    a shell,
    a slurry filler compartment interior to the shell containing slurry filler, a fluid compartment, the fluid compartment being deformable from a neutral profile under pressure from the slurry filler and which recoils to the neutral profile when not under pressure, a lens-shaped reservoir, the reservoir being disposed external to the shell, the reservoir and fluid compartment being fluidically coupled by a port, and a limiting membrane region disposed between the fluid compartment and the reservoir.

23. The implantable prosthesis of claim 22 wherein the shell comprises silicon elastomer.

24. The implantable prosthesis of claim 22 wherein the slurry filler is comprised of the group including medical glass toroids, spheres and amorphous glass "frit", having a combination of particles ranging in diameter from 500 microns to 2.0 mm, resembling a powder suspended in normal saline.

25. The implantable prosthesis of claim 22 wherein the slurry filler is comprised of the group including biopolymer toroids, spheres and amorphous glass "frit", having a combination of particles ranging in diameter from 500 microns to 2.0 mm, resembling a powder suspended in normal saline.

26. The implantable prosthesis of claim 22 wherein the slurry comprises particulate elements of a number of differing diameters such that "nesting" or "closest packing" defines their spatial relationship.

27. The implantable prosthesis of claim 22 wherein the fluid compartment has a fluid capacity of approximate 20-35% of the fluid volume of the whole implant.

28. The implantable prosthesis of claim 22 having a shape calibrated to resist excessive deformation and also the capacity to bleed-off or transfer fluid from inside the implant to a lens-shaped reservoir outside the implant.

29. The implantable prosthesis of claim 22 wherein the reservoir contains normal saline and communicates freely with the fluid compartment via a tube and the reservoir being lens-shaped and located below and outside the implant.

30. The implantable prosthesis of claim 22 wherein the fluid compartment has a unique fillport being a targetable depression located at the central apex of the fluid compartment, which point is capable of being penetrated by a hollow hypodermic needle to enable the introduction of normal saline into the buttress and also to extract any unwanted gas contained therein.

31. An implantable mammary prosthesis comprising:
a shell,
a slurry filler compartment interior to the shell containing slurry filler,
a fluid compartment, the fluid compartment being deformable from a neutral profile under pressure from the slurry filler and which recoils to the neutral profile when not under pressure, the fluid compartment including a modulating buttress,
a reservoir, the reservoir being disposed external to the shell, the reservoir and fluid compartment being fluidically coupled by a port, and
a limiting membrane region disposed between the fluid compartment and the reservoir.

32. The implantable prosthesis of claim 31 wherein the shell comprises silicon elastomer.

33. The implantable prosthesis of claim 31 wherein the slurry filler is comprised of the group including medical glass toroids, spheres and amorphous glass "frit", having a combination of particles ranging in diameter from 500 microns to 2.0 mm, resembling a powder suspended in normal saline.

34. The implantable prosthesis of claim 31 wherein the slurry comprises normal saline and chemically etched or silver plated particulate solids.

35. The implantable prosthesis of claim 31 wherein the slurry has a high ratio of medical glass particulate solids to normal saline so as to have a high viscosity resembling that of silicone elastomer gel or thick toothpaste.

36. The implantable prosthesis of claim 31 wherein the slurry filler is comprised of the group including biopolymer toroids, spheres and amorphous glass 'frit", having a combination of particles ranging in diameter from 500 microns to 2.0 mm, resembling a powder suspended in normal saline.

37. The implantable prosthesis of claim 31 wherein the fluid compartment comprises a buttress consisting of a sessile hollow ovoid structure which is adherently located internally at the base pole of the implant and which is rigid or relatively deformable and compliant by changing the fluid volume contained within it.

38. The implantable prosthesis of claim 37, wherein the fluid compartment is made from a silicone elastomer molding with the necessary structural resiliency providing a high degree of recoil, and having a void within it which is in fluid communication with a reservoir.

39. The implantable prosthesis of claim 37 wherein the slurry filler compartment and the fluid compartment buttress share a fluid access portal via the apical fillport and furthermore the buttress having a needle access point at the depression at the apex of the buttress and each having its own specified fluid.

40. The implantable prosthesis of claim 39 wherein the apical fillport includes a large enough diameter to permit the tubular introduction of the slurry.

41. The implantable prosthesis of claim 37 wherein the buttress serves as a major conditioner-modulator of the overall viscosity of the slurry filler by serving as a buttress against which induced fluid pressure waves in the implant are accelerated or retarded by virtue of its relative profile and susceptibility to deformation, or lack thereof, and which functions also to enable it to transfer to, or aspirate quantities of contained normal saline from an external reservoir adjoining the implant.

* * * * *